US008865177B2

(12) United States Patent
First

(10) Patent No.: US 8,865,177 B2
(45) Date of Patent: Oct. 21, 2014

(54) PRESSURE SORE TREATMENT

(75) Inventor: Eric R. First, Boston, MA (US)

(73) Assignee: Allergan, Inc., Irvine, CA (US)

( * ) Notice: Subject to any disclaimer, the term of this patent is extended or adjusted under 35 U.S.C. 154(b) by 184 days.

(21) Appl. No.: 11/932,908

(22) Filed: Oct. 31, 2007

(65) Prior Publication Data

US 2008/0050404 A1   Feb. 28, 2008

Related U.S. Application Data

(63) Continuation of application No. 10/814,764, filed on Mar. 31, 2004, now abandoned.

(51) Int. Cl.
| A61K 39/00 | (2006.01) |
| A61K 39/38 | (2006.01) |
| A61K 39/08 | (2006.01) |
| A61K 38/00 | (2006.01) |
| A01N 63/00 | (2006.01) |
| A61P 17/00 | (2006.01) |
| A61K 38/48 | (2006.01) |

(52) U.S. Cl.
CPC .................................. *A61K 38/4893* (2013.01)
USPC ............... 424/184.1; 424/247.1; 424/239.1; 424/167.1; 424/93.41; 514/18.6

(58) Field of Classification Search
CPC ............................................. A61K 39/08
USPC .................................................... 424/239.1
See application file for complete search history.

(56) References Cited

U.S. PATENT DOCUMENTS

| 4,805,605 | A | * | 2/1989 | Glassman ........................ 602/24 |
| 5,437,291 | A | | 8/1995 | Pasricha et al. ............... 128/898 |
| 5,670,484 | A | | 9/1997 | Binder ............................ 514/14 |
| 5,714,468 | A | | 2/1998 | Binder ............................ 514/14 |
| 5,766,605 | A | | 6/1998 | Sanders et al. ............. 424/239.1 |
| 5,989,545 | A | | 11/1999 | Foster et al. ................ 424/183.1 |
| 6,063,768 | A | | 5/2000 | First ................................ 514/14 |
| 6,087,327 | A | * | 7/2000 | Pearce et al. ...................... 514/2 |
| 6,139,845 | A | | 10/2000 | Donovan ..................... 424/236.1 |
| 6,299,893 | B1 | | 10/2001 | Schwartz et al. ............. 424/422 |
| 6,306,423 | B1 | | 10/2001 | Donovan et al. ............. 424/423 |
| 6,312,708 | B1 | | 11/2001 | Donovan ....................... 424/423 |
| 6,423,319 | B1 | * | 7/2002 | Brooks et al. ............. 424/239.1 |
| 6,447,787 | B1 | * | 9/2002 | Gassner et al. ............. 424/247.1 |
| 6,458,365 | B1 | | 10/2002 | Aoki et al. ................. 424/239.1 |
| 6,464,986 | B1 | | 10/2002 | Aoki et al. ................. 424/239.1 |
| 6,503,539 | B2 | * | 1/2003 | Gestrelius et al. ............ 424/549 |
| 2002/0187164 | A1 | * | 12/2002 | Borodic ...................... 424/247.1 |
| 2002/0192239 | A1 | | 12/2002 | Borodic et al. ............. 424/247.1 |
| 2003/0021776 | A1 | * | 1/2003 | Rebar et al. ................. 424/94.63 |
| 2003/0036502 | A1 | * | 2/2003 | Gassner et al. .................... 514/2 |
| 2003/0224019 | A1 | | 12/2003 | O'Brien ...................... 424/239.1 |
| 2004/0009180 | A1 | | 1/2004 | Donovan .................... 424/184.1 |
| 2004/0167223 | A1 | * | 8/2004 | Popp ............................. 514/568 |
| 2004/0175445 | A1 | * | 9/2004 | Hnat ............................. 424/735 |
| 2005/0123567 | A1 | * | 6/2005 | First ........................... 424/239.1 |
| 2005/0196414 | A1 | * | 9/2005 | Dake et al. ................. 424/239.1 |
| 2006/0039930 | A2 | * | 2/2006 | Gassner et al. ............ 424/239.1 |
| 2006/0067950 | A1 | * | 3/2006 | Taylor ........................ 424/239.1 |
| 2006/0259995 | A1 | * | 11/2006 | Cayouette et al. .............. 800/18 |
| 2007/0280970 | A1 | * | 12/2007 | Wilson ....................... 424/282.1 |
| 2009/0053283 | A1 | * | 2/2009 | Rothbard et al. .............. 424/423 |
| 2010/0280488 | A1 | * | 11/2010 | Pruitt et al. .................... 604/506 |
| 2013/0203809 | A1 | * | 8/2013 | Dibas et al. .................... 514/314 |

FOREIGN PATENT DOCUMENTS

| WO | WO 00/24419 | * | 5/2000 |
| WO | WO 03/011333 | | 2/2003 |

OTHER PUBLICATIONS

Brisinda, Giuseppe et al, 1999, vol. 341, No. 2, pp. 65-69, The New England Journal of Medicine, Jul. 8, 1999, A Comparison of injections of Botulinum toxin and topical nitroglycerin ointment for the treatment of chronic anal fissure.*
Brin, Mitchell F. and the Spasticity Study Group, 1997, Supplement 6, pp. S208-S220, Dosing and administration.*
Brin, Mitchell F., MD, Botulinum Toxin: Chemistry, Pharmacology, Toxicity and Immunology, pp. S146-S168, Muscle & Nerve Supplement 6, The Pharmacology of Botulinum toxin, (1997).*
Brisinda et al, reference of record.*
Sloop, R. Richard et al, Movement Disorders, vol. 16(1), 2001, pp. 100-105, Muscle Paralysis produced by botulinum toxin Type A injection in treated torticollis patients compared with toxin naïve individuals.*
Kennedy M. "Rehabilitation medicine offers the best of old and new" Wisconsin Med Journal 1997, vol. 96, No. 12 pp. 21.
Voller B. et al. "Treatment of the spastic drop foot with botulinum toxin type A in adult patients" 2001, vol. 113 Suppl 4, pp. 25-29.
Dykstra, D., *Botulinum toxin type B for gait and AFO fit improvement in post-CVS spasticity*, Arch. Pharrrvacol., 365, Suppl. 2, R18, 38.
Andreadis S., et al., *Keratinocyte growth factor induces hyperproliferation and delays differsntiation in a skin equivalent model system*, Faseb J. Apr. 2001;15(6):898-906.

(Continued)

*Primary Examiner* — Albert Navarro
*Assistant Examiner* — Ginny Portner
(74) *Attorney, Agent, or Firm* — Brigitte C. Phan; Ted Chan; Debra Condino

(57) ABSTRACT

Methods for treating a pressure sore or for preventing development of a pressure sore by local administration of a Clostridial toxin, such as a botulinum neurotoxin, to a pressure sore or to a pressure point, or to the vicinity thereof.

4 Claims, 1 Drawing Sheet

(56) References Cited

OTHER PUBLICATIONS

Aoki K., et al, *Mechanisms of the antinociceptive effect of subcutaneous Botox: Inhibition of peripheral and central nociceptive processing*, Cephalalgia Sep. 2003;23(7):649.

Arredondo J., et al., *Central role of alpha7 nicotinic receptor in differentiation of the stratified squamous epithelium*, J Cell Biol. Oct. 28, 2002;159(2):325-36.

Asahina A., et al., *Specific induction of cAMP in Langerhans cells by calcitonin gene-related peptide: relevance to functional effects*, Proc Natl Acad Sci USA. Aug. 29, 1995;92(18):8323-7.

Bigaike H., et al., *Botulinum A Neurotoxin Inhibits Non-Cholinergic Synaptic Transmission in Mouse Spinal Cord Neurons in Culture*, Brain Research 360;318-324:1985.

Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316;244-251:1981.

Binz T., et al., *The Complete Sequence of Botulinum Neurotoxin Type A and Comparison with Other Clostridial Neurotoxins*, J Biological Chemistry 265(16);9153-9158:1990.

Blugerman G., et al, *Multiple eccrine hidrocystomas: A new therapeutic option with botulinum toxin*, Dermatol Surg May 2003;29(5):557-9.

Borodic, Gary E., et al., *Pharmacolo and Histology of the Therapeutic Application of Botulinum Toxin*, from Therapy with Botulinum Toxin, Ed. Jankovic J. et al., Marcel Dekker, Inc., (1994), p. 150.

Brem, H., et al, *Placebo-Controlled Trial of Safety and Efficacy of Intraoperative Controlled Delivery by Biodegradable Polymers of Chemotherapy for Recurrent Gliomas*, Lancet 345;1008-1012:1995.

Bushara K., *Botulinum toxin and rhinorrhea*, Otolaryngol Head Neck Surg 1996;114(3):507.

Chen W., et al., *Trophic interactions between sensory nerves and their targets*, Journal of Biomedical Science. 1999;6(2):79-85.

Chiang H-Y., et al., *Regional difference in epidermal thinning after skin denervation*, Exp Neural 1998;154(1):137-45.

Coffield J., et al., *The Site and Action of Botulinum Neuro-Toxin*, from Therapy with.Botulinum Toxin, Ed. Jankovic J. et al., Marcel Dekker, Inc., (1994), p. 5.

Dabrowski E., et al, *Botulinum toxin as a novel treatment for self mutilation in Lesch-Nyhan syndrome*, Ann Neurol Sep. 2002;52(3 Supp 1):S157.

Fung L. K., et al., *Pharmacokinetics of Interstitial Delivery of Carmustine 4-Hydroperoxycyclophosphamide and Paclitaxel From a Biodegradable Polymer Implant in the Monke Brain*, Cancer Research 58;672-684:1998.

Gonelle-Gispert, Carmen, et al., *SNAP-25a and -25b Isoforms are Both Expressed in Insulin-Secreting Cells and Can Function in Insulin Secretion*, Biochem J. (1999) 339 (pt 1); pp. 159-65.

Grando S., *Biological functions of keratinocyte cholinergic receptors*, J Investig Dermatol Symp Proc. Aug. 1997; 2(1):41-8.

Grando S., et al., *Activation of keratinocyte nicotinic cholinergic receptors stimulates calcium influx and enhances cell differentiation*, Invest Dermatol. Sep. 1996;107(3):412-8.

Grando S., et al., *Human keratinocytes synthesize, secrete, and degrade acetylcholine* J Invest Dermatol. Jul. 1993;101(1):32-6.

Grando S., at al., *Keratinocyte muscarinic acetylcholine receptors: immunolocalization and partial characterization*, J Invest Dermatol. Jan. 1995;104(1):95-100.

Griffin John W., et al., *Axonal Degeneration and Disorders of the Axonal Cytoskeleton, The Axon*, Ed. Waxman S., et al., New York: Oxford University.Press, 1995; pp. 375-390.

Habermann E., et al., *Tetanus Toxin and Botulinum A and C Neurotoxins Inhibit Noradrenaline Release From Cultured Mouse Brain*, J Neurochem 51(2);522-527:1988.

Habermann E., *I-Labeled Neurotoxin from Clostridium Botulinum A: Preparation, Binding to Synaptosomes and Ascent to the Spinal Column*, Naunyn-Schmiedeberg's Arch. Pharmacol. 1974; 281, pp. 47-56.

Habermann E., *Inhibition by Tetanus and Botulinum A Toxin of the release of [3H]Noradrenaline and [3H]GABA From Rat Brain Homogenate*, Experientia 44;224-226:1988.

*Harrison's Principles of Internal Medicine* (1998), edited by Anthony Fauci et al., 14th edition, published by McGraw Hill.

Heckmann M., et al., *Botulinum toxin type A injection in the treatment of lichen simplex: An open pilot study*, J Am Acad Dermatol Apr. 2002;46(4):617-9.

Hokffelt T., *Neuropeptides in perspective : The last ten years*, Neuron 1991; 7: 867-879.

Hosoi J., et al., *Regulation of Langerhans cell function by nerves containing calcitonin gene-related peptide*, Nature. May 13, 1993;363(6425):159-63.

Hsieh S., at al., *Epidermal denervation and its effects on keratinocytes and Langerhans cells*, J Neurocytol 1996;25:513-524.

Hsieh S., et al., *Modulation of keratinocyte proliferation by skin innervation*. Journal of Investigative Dermatology, 1999;113(4):579-86.

Hsieh S., et al., *Pathology of nerve terminal degeneration in the skin*, Journal of Neuropathology & Experimental Neurology. 2000;59(4):297-307.

Hsieh S., et al., *Skin Innervation and Its Effects on the Epidermis*, J Biomed Sci. 1997;4(5):264-268.

Hsiung-F., et al., (2001) *Quantitative pathology of cutaneous nerve terminal degeneration in the human skin*, Acta Neuropathologica 102:455-461.

Huang T., et al., *Influence of cutaneous nerves on keratinocyte proliferation and epidermal thickness in mice*, Neuroscience 94 :965-973, 1999.

Inaba N., et al., *Capsaicin-induced calcitonin gene-related peptide release from isolated rat stomach measured with a new chemiluminescent enzyme immunoassay*, Jpn J Pharmacol. Nov. 1996;72(3):223-9.

Jacks L., et al., *Idiopathic toe walking: Treatment with botulinum toxin A injection*, Dev Med Child Neurol 2002;44(Suppl 91):6.

Johnson M., *Synaptic glutamate release by postnatal rat serotonergic neurons in microculture*, Neuron 1994; 12: 433-442.

Jost W., *Ten years' experience with botulinum toxin in anal fissure*, Int J Colorectal Dis Sep. 2002;17(5):298-302.

Kaneko T., et al., *Immunohistochemical demonstration of glutaminase in catecholaminergic and serotonergic neurons of rat brain*, Brain Res. 1990; 507: 141-154.

Kasakov L., et al., *Direct evidende for concomitant release of noradrenaline, adenosine 5'-triphosphate and neuropeptide Y from sympathetic nerve supplying the guinea-pig vas deferens*. J. Auton. Nerv. Syst. 1988; 22: 75-82.

Katsambas A., et al., *Cutaneous diseases of the foot: Unapproved treatments*, Clin Dermatol Nov.-Dec. 2002;20(6):689-699.

Ko M., et al., *Cutaneous nerve degeneration induced by acrylamide in mice*, Neuroscience Letters.(2000)293(3):195-8.

Komuves Laszlo et al., *Epidermal expression of the full-length extracellular calcium-sensing receptor is required for normal keratinocyte differentiation*, J. Cell Physiol. Jul. 2002;192(1); pp. 45-54.

Kmjevic K., *Central cholinergic mechanisms and function*. Prog Brain Res. 1993;98:285-92.

Kupfermann I., *Functional studies of cotransmission*, Physiol. Rev. 1991; vol. 71, No. 3, Jul. 1991; pp. 683-732.

Lee M., et al., *Clinical and electrophysiological characteristics of inflammatory demyelinating neuropathies*, Acta Neurol Taiwan 1997;6:283-288.

Legat F., et al., *Repeated subinflammatory ultraviolet B irradiation increases substance P and calcitonin gene-related peptide content and augments mustard oil-induced neurogenic inflammation in the skin of rats*, Neurosci Lett. Sep. 6, 2002;329(3):309-13.

Li Y., et al., *Sensory and motor denervation influences epidermal thickness in rat foot glabrous skin*, Exp Neurol 1997;147:452-462 (see p. 459).

Lin Y., et al., (2001) *Cutaneous nerve terminal degeneration in painful mononeuropsthy*, Experimental Neurology. 170(2):290-6.

Lin Y., et al., *Quantitative sensory testing: normative values and its application in diabetic neuropathy*, Acta Neurol Taiwan 1998;7:176-184.

(56) References Cited

OTHER PUBLICATIONS

Lundberg J., *Pharmacology of cotransmission in the autonomic nervous system: Integrative aspects on amines, neuropeptides, adenosine triphosphate, amino acids and nitric oxide*, Pharmacol. Rev. 1996; 48: 113-178.

Marchese-Ragona, Rosario, et al., *Management of Parotid Sialocele with Botulinum Toxin*, The Laryngoscope 109:1344-1346:1999.

McCarthy B., et al., *Cutaneous innervation in sensory neuropathies: evaluation by skin biopsy*, Neurol 1995;45:1848-1855.

*Mov Disord*, 10(3):376:1995.

Moyer E. et al., *Botulinum Toxin Type B: Experimental and Clinical Experience*, being chapter 6, pp. 71-85 of "Therapy With Botulinum Toxin", edited by Jankovic, J. et al. (1994), Marcel Dekker, Inc.

Naumann, Markus, et al., *Botulinum Toxin Type A in the Treatment of Focal, Axillary and P !mar Hyperhidrosis and Other Hyperhidnatic Conditions*, European J. Neurology 6 (Supp 4): S111-S1150:1999.

Ndoye A., et al., *Identification and mapping of keratinocyte muscarinic acetylcholine receptor subtypes in human epidermis*, J Invest Dermatol. Sep. 1998;111(3):410-6.

Nguyen V., et al., *Keratinocyte acetylcholine receptors regulate cell adhesion* Life Sci. Mar. 28, 2003; 72(18-19):2081-5.

Nguyen V., et al., *Programmed cell death of keratinocytes culminates in apoptotic secretion of a humectant upon secretagogue action of acetylcholine* J Cell Sci. Mar. 2001:114(Pt 6):1189-204.

Nicholas A., at al., *Glutamate-like immunoreactivity in medulla oblongata catecholamine/substance P neurons*, NeuroReport 1990; 1: 235-238.

Nicholas A., et al., *Serotonin-, Substance P- and Glutamae/Aspartate-like Immunoreactivities in Medullo-Spinal Pathways of Rat and Primate*, Neuroscience, vol. 48, No. 3, pp. 545-559.

Palacios J., et al., *Cholinergic neuropharmacology: an update*, Acta Psychiatr Scand Suppl. 1991;366:27-33.

Pan C., et al., (2001) *Degeneration of nociceptive nerve terminals in human peripheral neuropathy*, Neuroreport. 12(4):787-92.

Pearce L.B., *Pharmacologic Characterization of Botulinum Toxin for Basic Science and Medicine*, Toxicon 35(9);1373-1412 at 1393.

Rogers J., et al., *Injections of botulinum toxin A in foot dystonia*, Neurology Apr. 1993;43(4 Suppl 2).

Sanchez-Prieto J., et al., *Botulinum Toxin A Blocks Glutamate Exocytosis From Guinea Pig Cerebral Cortical Synaptosomes*, Eur J. Biochem 165;675-681:1897.

Schantz E.J., et al, *Properties and use of Botulinum toxin and Other Microbial Neurotoxins in Medicine*, Microbiol Rev. 56;80-99:1992.

Sevim S., et al., *Botulinum toxin-A therapy for palmar and plantar hyperhidrosis*, Acta Neural Beig Dec. 2002:102(4):1 67-70.

Singh, *Critical Aspects of Bacterial Protein Toxins*, pp. 63-84 (chapter 4) of Natural Toxins II, edited by B.R. Singh et al., Plenum Press, New York (1976).

Sloop, R. Richard, et al., *Reconstituted Botulinum Toxin Type A Does Not Lose Potency in Humans if it is Refrozen or Refrigerated for 2 Weeks Before Use*, Neurology, 48:249-53:1997.

Sneddon P., et al., *Pharamcological evidence that adenosine triphosphate and noradrenaline are cotransmitters in the guinea-pig vas deferens*. J. Physiol. 1984; 347: 561-580.

Suputtitada A., *Local botulinum toxin type A injections in the treatment of spastic toes*, Am J Phys Med Rehabil Oct. 2002:81(10):770-5.

Weigand at al, *Nauny-Schmiedeberg's Arch. Pharmacol.* 1976; 292, 161-165.

Whitehouse P., et al., *Nicotinic and muscarinic cholinergic receptors in Alzheimer's disease and related disorders*, J Neural Transm Suppl. 1987;24:175-82.

Wu T., et al., *Demonstration of human papillomavirus (HPV) genomic amplification and viral-like particles from CaSki cell line in SCID mice*, J Virol Methods 1997;65:287-298.

Xu Z-Qd., et al, *Galanin/GMAP—and NPY-like immunoreactivities in locus coeruleus and noradrenergic nerve terminals in the hippocampal formation and cortex with notes on the galanin-R1 and—R2 receptors*, J. Comp. Neural. 1998; 392: 227-252.

Xu Z-Qd., et al., *Galanin-5-hydroxytryptamine interactions: Electrophysiological, immunohistochemical and in situ hybridization studies on rat dorsal raphe neurons with a note on galanin R1 and R2 receptors*. Neuroscience 1998; 87: 79-94.

Zia S., et al., *Receptor-mediated inhibition of keratinocyte migration by nicotine involves modulations of calcium influx and intracellular concentration*, J Pharmacol Exp Ther. Jun. 2000;293(3):973-81.

\* cited by examiner

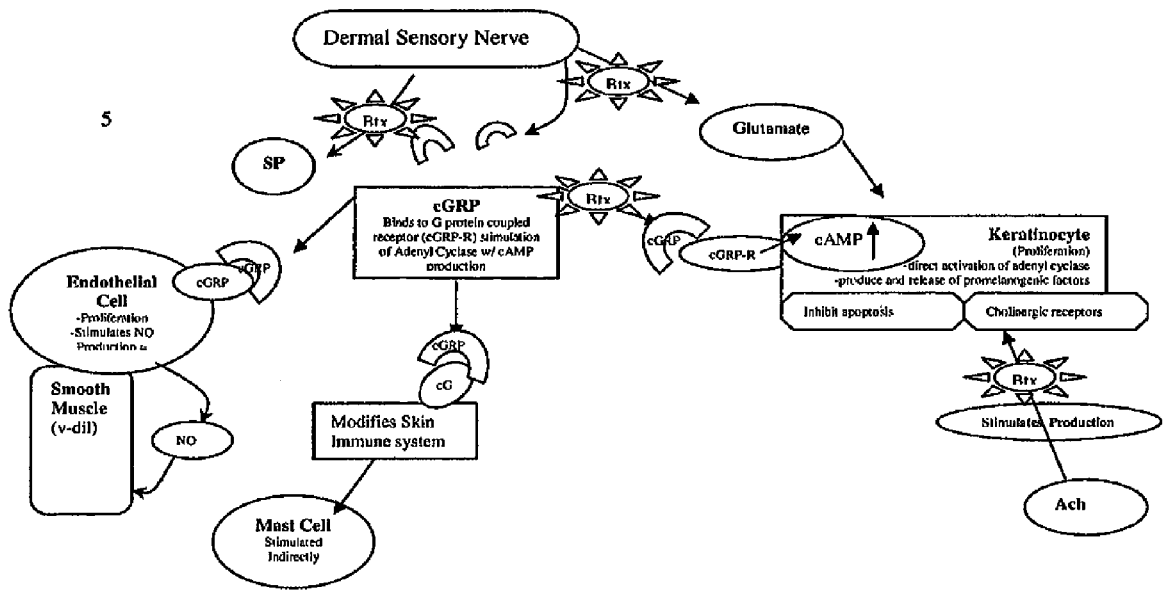

PRESSURE SORE TREATMENT

CROSS REFERENCE TO RELATED APPLICATIONS

This application is a continuation of U.S. patent application Ser. No. 10/814,764 filed on Mar. 31, 2004, the entire disclosure of which is incorporated herein by reference.

BACKGROUND

The present invention relates to methods for treating pressure sores. In particular the present invention relates to methods for treating pressure sores by administration of a Clostridial neurotoxin to a patient.

Pressure sores include bed sores, decubitus ulcers and ischial tuberosity ulcers and can cause considerable pain and discomfort to a patient. A pressure sore can occur as a result of a prolonged pressure applied to the skin. Thus, pressure can be exerted on the skin of a patient due to the weight or mass of an individual. The pressure exerted can be in excess of the capillary filling pressure which is approximately 32 mm Hg. A pressure sore can develop when blood supply to an area of the skin is obstructed or cut off for more than two or three hours. The affected skin area can turns red, becomes painful and die. If untreated, the skin breaks open and can become infected. A pressure sore is therefore a skin ulcer that occur in an area of the skin that is under pressure from e.g. lying in bed, sitting in a wheelchair, and/or wearing a cast for a prolonged period of time. Pressure sores can occur when a person is bedridden, unconscious, unable to sense pain, or immobile. Pressure sores often occur in the buttocks area (on the sacrum or iliac crest), or on the heels of foot.

In patients with normal sensitivity, mobility, and mental faculty, pressure sores usually do not occur. Thus, feedback, both conscious and unconscious, from the areas of compression normally leads the individual to change his body position and such body position changes relieve the pressure prior to a tissue damage and development of a pressure sore.

Individuals unable to avoid long periods of uninterrupted pressure to the skin over bony prominences are at an increased risk for the development of necrosis and ulceration, that is development of a pressure sore. This group of patients typically includes elderly individuals, the neurologically impaired, and hospitalized patients. Often these individuals cannot protect themselves from the pressure exerted on their bodies unless they consciously change position or have assistance in doing so. Even the most conscientious patient with an extensive support group and unlimited financial resources can develop ulceration resulting from a brief lapse in avoidance of the ill effects of pressure.

Of the various factors which can contribute to the development of a pressure sore, pressure leading to ischemia (a local anemia due to mechanical obstruction of a blood supply) is a final common pathway. Skin tissues are capable of withstanding enormous pressures when brief in duration, but prolonged exposure to pressures slightly above capillary filling pressure initiates a downward spiral towards the ulceration characteristic of a pressure sore.

Contractures and spasticity can contribute to the develop of a pressure sore by repeatedly exposing tissues to pressure through flexion of a joint. Contractures rigidly hold a joint in flexion, while spasticity subjects tissues to considerable repeated friction and shear forces.

While the inciting event in development of a pressure sore is compression of the skin by an external force such as a mattress, wheelchair pad, or bed rail, traumatic forces such as shear forces and friction can contribute. These forces cause microcirculatory occlusion as pressures rise above capillary filling pressure, resulting in ischemia. Ischemia leads to inflammation and tissue anoxia. Tissue anoxia leads to cell death, necrosis, and ulceration. Pressure on the skin can be greatest over a bony prominence.

It is generally accepted that there are four stages in the development of a pressure sore. In stage I the skin is intact but has signs of impending ulceration such as blanchable erythema (redness) of the skin which can resolve within 24 hours of relief of the pressure; Blanchable means that upon pressing the area of skin redness the redness can be decreased (blanched therefore). Stage I can also include non-blanchable skin erythema, which may be the first outward sign of tissue destruction. Alternately, the skin can appear white from ischemia.

In stage II there is a lesion which appears as a partial loss of skin involving the epidermis and possibly the dermis. This lesion can be present as an abrasion, blister, or superficial ulceration. In stage III there is a full-thickness loss of skin with extension into subcutaneous tissue but not through the underlying fascia. The stage III lesion presents as a crater with or without undermining of adjacent tissue.

Finally, in stage IV there is a full-thickness loss of skin and subcutaneous tissue and extension into muscle, bone, tendon, or joint capsule. Osteomyelitis with bone destruction, dislocations, or pathologic fractures can also be present. Sinus tracts and severe undermining can also be present.

Medical therapy to resolve a pressure sore is firstly to reduce or eliminate the causative pressure. Specialized support surfaces are available for bedding and wheelchairs, which can maintain tissues pressures below 30 mm Hg. These specialized surfaces include foam devices, air-filled devices, low-airloss beds (Flexicair, KinAir), and air-fluidized beds (Clinitron, FluidAir). Low-airloss beds support the patient on multiple inflatable air-permeable pillows. Air-fluidized beds suspend the patient as air is pumped into an air-permeable mattress containing millions of microspheric uniformly sized silicone-coated beads. All these devices have been shown to reduce tissue pressure over conventional hospital mattresses and wheelchair cushions.

Wound dressings vary with the state of the wound. A stage I lesion with signs of impending breakdown may require no dressing. Stage II ulcers confined to the epidermis or dermis may be treated with a hydrocolloid occlusive dressing (DuoDerm), which maintains a moist environment to facilitate reepithelialization. For more advanced ulcers, a large variety of treatment options is available. These include wet-to-dry dressings, incorporating isotonic sodium chloride solution or dilute. Dakins solution (sodium hypochlorite), Silvadene, Sulfamylon, hydrogels (Carrington gel), xerogels (Sorbsan), and vacuum-assisted closure (VAC) sponges. Daily whirlpool use also may serve to irrigate and mechanically debride the wound.

Spasticity can be relieved with diazepam, baclofen, dantrolene sodium, mephenesin carbonate, dimethothiazine, or orciprenaline. Flexion contractures can be relieved surgically.

Even with optimal medical management, a patient with pressure sores can require surgical debridement of the pressure sore, diversion of urinary or fecal stream, release of flexion contractures, wound closure, or amputation.

It has been estimated that the treatment of pressure sores in the United States costs in excess of one billion dollars a year. Two thirds of pressure sores occur in patients older than 70 years and the prevalence rate in nursing homes and long term care facilities can be as high as 30%. Patients who are neurologically impaired have a lifetime risk of developing pressure sores as high as 85%. Pressure sores have been stated to be the direct cause of death in about 8% of all paraplegics. Additionally, patients hospitalized with acute illness have an incidence rate of pressure sores of up to 11%. Disturbingly, even with current medical and surgical therapies, patients who achieve a healed pressure have recurrence rates as high as 90%.

Botulinum Toxin

The genus *Clostridium* has more than one hundred and twenty seven species, grouped according to their morphology and functions. The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and shows a high affinity for cholinergic motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (purified neurotoxin complex)[1] is a LD50 in mice (i.e. 1 unit). One unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63-84 (chapter 4) of Natural Toxins II, edited by B R. Singh et al., Plenum Press, New York (1976) (where the stated LD50 of botulinum toxin type A of 0.3 ng equals 1 U is corrected for the fact that about 0.05 ng of BOTOX® equals 1 unit). One unit (U) of botulinum toxin is defined as the LD50 upon intraperitoneal injection into female Swiss Webster mice weighing 18 to 20 grams each.

[1] Available from Allergan, Inc., or Irvine, Calif. under the tradename BOTOX® in 100 unit vials)

Seven generally immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate LD50 for botulinum toxin type A. Moyer E et al., *Botulinum Toxin Type B: Experimental and Clinical Experience*, being chapter 6, pages 71-85 of "Therapy With Botulinum Toxin", edited by Jankovic, J. et al. (1994), Marcel Dekker, Inc. Botulinum toxin apparently binds with high affinity to cholinergic motor neurons, is translocated into the neuron and blocks the release of acetylcholine. Additional uptake can take place through low affinity receptors, as well as by phagocytosis and pinocytosis.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain (the H chain or HC), and a cell surface receptor. The receptor is thought to be different for each type of botulinum toxin and for tetanus toxin. The carboxyl end segment of the HC appears to be important for targeting of the botulinum toxin to the cell surface.

In the second step, the botulinum toxin crosses the plasma membrane of the target cell. The botulinum toxin is first engulfed by the cell through receptor-mediated endocytosis, and an endosome containing the botulinum toxin is formed. The toxin then escapes the endosome into the cytoplasm of the cell. This step is thought to be mediated by the amino end segment of the HC, the HN, which triggers a conformational change of the toxin in response to a pH of about 5.5 or lower. Endosomes are known to possess a proton pump which decreases intra-endosomal pH. The conformational shift exposes hydrophobic residues in the toxin, which permits the botulinum toxin to embed itself in the endosomal membrane. The botulinum toxin (or at least the light chain of the botulinum) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc ($Zn^{++}$) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotype A and E cleave SNAP-25. Botulinum toxin serotype C1 was originally thought to cleave syntaxin, but was found to cleave syntaxin and SNAP-25. Each of the botulinum toxins specifically cleaves a different bond, except botulinum toxin type B (and tetanus toxin) which cleave the same bond. Each of these cleavages block the process of vesicle-membrane docking, thereby preventing exocytosis of vesicle content.

Botulinum toxins have been used in clinical settings for the treatment of neuromuscular disorders characterized by hyperactive skeletal muscles (i.e. motor disorders). In 1989 a botulinum toxin type A complex was approved by the U.S. Food and Drug Administration for the treatment of blepharospasm, strabismus and hemifacial spasm. Subsequently, a botulinum toxin type A was also approved by the FDA for the treatment of cervical dystonia and for the treatment of glabellar lines, and a botulinum toxin type B was approved for the treatment of cervical dystonia. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months, although significantly longer periods of therapeutic activity have been reported.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type C1 has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. *Biochem J* 1; 339 (pt 1): 159-65:1999, and *Mov Disord,* 10(3):376:1995 (pancreatic islet B cells contains at least SNAP-25 and synaptobrevin).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and C1 is apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin proteins and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when a botulinum toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain,* J Neurochem 51(2); 522-527:1988) CGRP, substance P and glutamate (Sanchez-Prieto, J., et al., *Botulinum Toxin A Blocks Glutamate Exocytosis From Guinea Pig Cerebral Cortical Synaptosomes,* Eur J. Biochem 165; 675-681:1897. Thus, when adequate concentrations are used, stimulus-evoked release of most neurotransmitters can be blocked by botulinum toxin. See e.g. Pearce, L. B., *Pharmacologic Characterization of Botulinum Toxin For Basic Science and Medicine,* Toxicon 35(9); 1373-1412 at 1393; Bigalke H., et al., *Botulinum A Neurotoxin Inhibits Non-Cholinergic Synaptic Transmission in Mouse Spinal Cord Neurons in Culture,* Brain Research 360; 318-324:1985; Habermann E., *Inhibition by Tetanus and Botulinum A Toxin of the release of [3H]Noradrenaline and [3H]GABA From Rat Brain Homogenate,* Experientia 44; 224-226:1988, Bigalke H., et al., *Tetanus Toxin and Botulinum A Toxin Inhibit Release and Uptake of Various Transmitters,* as Studied with Particulate Preparations From Rat Brain and Spinal Cord, Naunyn-Schmiedeberg's Arch Pharmacol 316; 244-251:1981, and; Jankovic J. et al., *Therapy With Botulinum Toxin,* Marcel Dekker, Inc., (1994), page 5.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes C1, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of *Clostridium botulinum* with characteristics of $\leq 3 \times 10^7$ U/mg, an A260/A278 of less than 0.60 and a distinct pattern of banding on gel electrophoresis. The known Shantz process can be used to obtain crystalline botulinum toxin type A, as set forth in Shantz, E. J., et al, *Properties and use of Botulinum toxin and Other Microbial Neurotoxins in Medicine,* Microbiol Rev. 56; 80-99:1992. Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kD molecular weight with a specific potency of $1-2 \times 10^8$ LD50 U/mg or greater; purified botulinum toxin type B with an approximately 156 kD molecular weight with a specific potency of $1-2 \times 10^8$ LD50 U/mg or greater, and; purified botulinum toxin type F with an approximately 155 kD molecular weight with a specific potency of $1-2 \times 10^7$ LD50 U/mg or greater.

Botulinum toxins and/or botulinum toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo. Pure botulinum toxin can also be used to prepare a pharmaceutical composition.

As with enzymes generally, the biological activities of the botulinum toxins (which are intracellular peptidases) is dependant, at least in part, upon their three dimensional conformation. Thus, botulinum toxin type A is detoxified by heat, various chemicals surface stretching and surface drying. Additionally, it is known that dilution of a botulinum toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the botulinum toxin may be used months or years after the toxin containing pharmaceutical composition is formulated, the toxin can be stabilized with a stabilizing agent such as albumin and gelatin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks. *Neurology,* 48:249-53:1997.

It has been reported that botulinum toxin type A has been used in clinical settings as follows:

(1) about 75-125 units of BOTOX® per intramuscular injection (multiple muscles) to treat cervical dystonia;

(2) 5-10 units of BOTOX® per intramuscular injection to treat glabellar lines (brow furrows) (5 units injected intramuscularly into the procerus muscle and 10 units injected intramuscularly into each corrugator supercilii muscle);

(3) about 30-80 units of BOTOX® to treat constipation by intrasphincter injection of the puborectalis muscle;

(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U (b) flexor digitorum sublimus: 7.5 U to 30 U (c) flexor carpi ulnaris: 10 U to 40 U (d) flexor carpi radialis: 15 U to 60 U (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

It is known that botulinum toxin type A can have an efficacy for up to 12 months (*European J. Neurology* 6 (Supp 4): S111-S1150:1999), and in some circumstances for as long as 27 months, when used to treat glands, such as in the treatment of hyperhydrosis. See e.g. Bushara K., *Botulitum toxin and rhinorrhea*, Otolaryngol Head Neck Surg 1996; 114(3):507, and *The Laryngoscope* 109:1344-1346.1999. However, the usual duration of an intramuscular injection of Botox® is typically about 3 to 4 months.

The success of botulinum toxin type A to treat a variety of clinical conditions has led to interest in other botulinum toxin serotypes. Two commercially available botulinum type A preparations for use in humans are BOTOX® available from Allergan, Inc., of Irvine, Calif., and Dysport® available from Beaufour Ipsen, Porton Down, England. A Botulinum toxin type B preparation (MyoBloc®) is available from Elan Pharmaceuticals of San Francisco, Calif.

In addition to having pharmacologic actions at the peripheral location, botulinum toxins may also have inhibitory effects in the central nervous system. Work by Weigand et al, *Nauny-Schmiedeberg's Arch. Pharmacol.* 1976; 292, 161-165, and Habermann, *Nauny-Schmiedeberg's Arch. Pharmacol.* 1974; 281, 47-56 showed that botulinum toxin is able to ascend to the spinal area by retrograde transport. As such, a botulinum toxin injected at a peripheral location, for example intramuscularly, may be retrograde transported to the spinal cord.

U.S. Pat. No. 5,989,545 discloses that a modified clostridial neurotoxin or fragment thereof, preferably a botulinum toxin, chemically conjugated or recombinantly fused to a particular targeting moiety can be used to treat pain by administration of the agent to the spinal cord.

A botulinum toxin has also been proposed for or has been used to treat skin wounds (U.S. Pat. No. 6,447,787), various autonomic nerve dysfunctions (U.S. Pat. No. 5,766,605), tension headache, (U.S. Pat. No. 6,458,365), migraine headache pain (U.S. Pat. No. 5,714,468), post-operative pain and visceral pain (U.S. Pat. No. 6,464,986), hair growth and hair retention (U.S. Pat. No. 6,299,893), psoriasis and dermatitis (U.S. Pat. No. 5,670,484), injured muscles (U.S. Pat. No. 6,423,319) various cancers (U.S. Pat. No. 6,139,845), smooth muscle disorders (U.S. Pat. No. 5,437,291), nerve entrapment syndromes (U.S. patent application 2003 0224019), acne (WO 03/011333) and neurogenic inflammation (U.S. Pat. No.

6,063,768). Controlled release toxin implants are known (see e.g. U.S. Pat. Nos. 6,306,423 and 6,312,708) as is transdermal botulinum toxin administration (U.S. patent application Ser. No. 10/194805).

It is known that a botulinum toxin can be used to: weaken the chewing or biting muscle of the mouth so that self inflicted wounds and resulting ulcers can heal (Payne M., et al, *Botulinum toxin as a novel treatment for self mutilation in Lesch-Nyhan syndrome*, Ann Neurol September 2002; 52(3 Supp 1):S157); permit healing of benign cystic lesions or tumors (Blugerman G., et al., *Multiple eccrine hidrocystomas: A new therapeutic option with botulinum toxin*, Dermatol Surg May 2003; 29(5):557-9); treat anal fissure (Jost W., *Ten years' experience with botulinum toxin in anal fissure*, Int J Colorectal Dis September 2002; 17(5):298-302, and; treat certain types of atopic dermatitis (Heckmann M., et al., *Botulinum toxin type A injection in the treatment of lichen simplex: An open pilot study*, J Am Acad Dermatol April 2002; 46(4):617-9).

Additionally, a botulinum toxin may have an effect to reduce induced inflammatory pain in a rat formalin model. Aoki K., et al, *Mechanisms of the antinociceptive effect of subcutaneous Botox; Inhibition of peripheral and central nociceptive processing*, Cephalalgia September 2003; 23(7):649. Furthermore, it has been reported that botulinum toxin nerve blockage can cause a reduction of epidermal thickness. Li Y, et al., *Sensory and motor denervation influences epidermal thickness in rat foot glabrous skin*, Exp Neurol 1997; 147:452-462 (see page 459). Finally, it is known to administer a botulinum toxin to the foot to treat excessive foot sweating (Katsambas A., et al., *Cutaneous diseases of the foot: Unapproved treatments*, Clin Dermatol November-December 2002; 20(6):689-699; Sevim, S., et al., *Botulinum toxin-A therapy for palmar and plantar hyperhidrosis*, Acta Neurol Belg December 2002; 102(4):167-70), spastic toes (Suputtitada, A., *Local botulinum toxin type A injections in the treatment of spastic toes*, Am J Phys Med Rehabil October 2002; 81(10):770-5), idiopathic toe walking (Tacks, L., et al., *Idiopathic toe walking: Treatment with botulinum toxin A injection, Dev* Med Child Neurol 2002; 44(Suppl 91):6), and foot dystonia (Rogers J., et al., *Injections of botulinum toxin A in foot dystonia*, Neurology April 1993; 43(4 Suppl 2)).

Tetanus toxin, as wells as derivatives (i.e. with a non-native targeting moiety), fragments, hybrids and chimeras thereof can also have therapeutic utility. The tetanus toxin bears many similarities to the botulinum toxins. Thus, both the tetanus toxin and the botulinum toxins are polypeptides made by closely related species of *Clostridium* (*Clostridium tetani* and *Clostridium botulinum*, respectively). Additionally, both the tetanus toxin and the botulinum toxins are dichain proteins composed of a light chain (molecular weight about 50 kD) covalently bound by a single disulfide bond to a heavy chain (molecular weight about 100 kD). Hence, the molecular weight of tetanus toxin and of each of the seven botulinum toxins (non-complexed) is about 150 kD. Furthermore, for both the tetanus toxin and the botulinum toxins, the light chain bears the domain which exhibits intracellular biological (protease) activity, while the heavy chain comprises the receptor binding (immunogenic) and cell membrane translocational domains.

Further, both the tetanus toxin and the botulinum toxins exhibit a high, specific affinity for gangliocide receptors on the surface of presynaptic cholinergic neurons. Receptor mediated endocytosis of tetanus toxin by peripheral cholinergic neurons results in retrograde axonal transport, blocking of the release of inhibitory neurotransmitters from central synapses and a spastic paralysis. Contrarily, receptor mediated endocytosis of botulinum toxin by peripheral cholinergic neurons results in little if any retrograde transport, inhibition of acetylcholine exocytosis from the intoxicated peripheral motor neurons and a flaccid paralysis.

Finally, the tetanus toxin and the botulinum toxins resemble each other in both biosynthesis and molecular architecture. Thus, there is an overall 34% identity between the protein sequences of tetanus toxin and botulinum toxin type A, and a sequence identity as high as 62% for some functional domains. Binz T. et al., *The Complete Sequence of Botulinum Neurotoxin Type A and Comparison with Other Clostridial Neurotoxins*, J Biological Chemistry 265(16); 9153-9168: 1990.

Acetylcholine

Typically only a single type of small molecule neurotransmitter is released by each type of neuron in the mammalian nervous system, although there is evidence which suggests that several neuromodulators can be released by the same neuron. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the bag 1 fibers of the muscle spindle fiber, by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

What is needed therefore is a therapeutically effective method for treating pressure sores.

SUMMARY

The present invention meets this need and provides methods for effectively treating a pressure sore by local administration of a Clostridial neurotoxin.

A method within the scope of the present invention for treating a pressure sore can have the step of local administration of a Clostridial neurotoxin to a pressure sore or to the vicinity of a pressure sore of a patient, thereby treating the pressure sore. In the vicinity of a pressure sore means within about 10 cm of the pressure sore. The pressure sore can be treated by reducing the size of (i.e. facilitating healing) the pressure sore, by reducing pain associated with the pressure sore and/or by reducing an inflammation associated with the pressure sore.

My invention also encompasses a method for preventing development or for preventing further development of a pressure sore by local administration of a botulinum neurotoxin to (or to the vicinity of) a pressure point. A pressure point is merely a dermal area upon which a patient exerts pressure for a prolonged period (i.e. for 2 hours or more hours). Thus an immobilized patient typically will typically have pressure points on his buttocks, shoulders and heels.

The neurotoxin can be locally administered in an amount of between about $10^{-3}$ units/kg of patient weight and about 35 units/kg of patient weight. Preferably, the neurotoxin is locally administered in an amount of between about $10^{-2}$ U/kg and about 25 U/kg of patient weight. More preferably, the neurotoxin is administered in an amount of between about $10^{-1}$ U/kg and about 15 U/kg. In a particularly preferred method within the scope of the present invention, the neurotoxin is locally administered in an amount of between about 1 U/kg and about 10 U/kg. In a clinical setting it can be advantageous to inject from 1 U to 3000 U of a neurotoxin, such as botulinum toxin type A or B, to a pressure sore location by topical application or by subdermal administration, to effectively treat the pressure sore.

A suitable neurotoxin for use in the practice of the present invention can be made by a Clostridial bacterium, such as *Clostridium botulinum*, *Clostridium butyricum* or *Clostridium beratti*. The neurotoxin use can be a modified neurotoxin, that is a neurotoxin has had at least one of its amino acids deleted, modified or replaced, as compared to a native neurotoxin. Additionally, the neurotoxin can be recombinantly made produced neurotoxin or a derivative or fragment of a recombinant made neurotoxin. The neurotoxin can be a botulinum toxin, such as one of the botulinum toxin serotypes A, B, $C_1$, D, E, F or G. A preferred botulinum toxin to use in the practice of the present invention is botulinum toxin type A.

A method according to my invention can be carried out by administration of a Clostridial toxin to a patient with, or who is predisposed to developing, a pressure sore. The Clostridial toxin used is preferably a botulinum toxin (as either a complex or as a pure [i.e. about 150 kDa molecule], such as a botulinum neurotoxin A, B, C1, D, E, F or G. Administration of the Clostridial toxin can be by a transdermal route (i.e. by application of a Clostridial toxin in a cream, patch or lotion vehicle), subdermal route (i.e. subcutaneous or intramuscular) or intradermal route of administration.

Except when treating a pressure sore related to contractures or spasticity, the dose of a Clostridial toxin used according to the present invention is less than the amount of toxin that would be used to paralyze a muscle, since the intent of a method according to the present invention is not to paralyze a muscle but to treat a pressure sore.

The following definitions apply herein:

"About" means approximately or nearly and in the context of a numerical value or range set forth herein means±10% of the numerical value or range recited or claimed.

"Alleviating" means a reduction in the occurrence of a pressure sore symptom. Thus, alleviating includes some reduction, significant reduction, near total reduction, and total reduction of a pressure sore symptom. An alleviating effect may not appear clinically for between 1 to 7 days after administration of a Clostridial neurotoxin to a patient.

"Botulinum toxin" means a botulinum neurotoxin as either pure toxin (i.e. about 150 kDa weight molecule) or as a complex (i.e, about 300 to about 900 kDa weight complex comprising a neurotoxin molecule and one or more associated non-toxic molecules), and excludes botulinum toxins which are not neurotoxins such as the cytotoxic botulinum toxins C2 and C3, but includes recombinantly made, hybrid, modified, and chimeric botulinum toxins.

"Local administration" or "locally administering" means administration (i.e. by a subcutaneous, intramuscular, subdermal or transdermal route) of a pharmaceutical agent to or to the vicinity of a dermal or subdermal location of a patient at the site of or in the vicinity of the site of a target skin area to be treated.

"Treating" means to alleviate (or to eliminate) at least one symptom of a pressure sore, either temporarily or permanently.

The Clostridial neurotoxin is administered in a therapeutically effective amount to alleviate a symptom of a pressure sore. A suitable Clostridial neurotoxin may be a neurotoxin made by a bacterium, for example, the neurotoxin may be made from a *Clostridium botulinum*, *Clostridium butyricum*, or *Clostridium beratti*. In certain embodiments of the invention, the pressure sore can be treated by applying to (topical) or into (intra or transdermal) the skin of a patient a botulinum toxin. The botulinum toxin can be a botulinum toxin type A, type B, type C1, type D, type E, type F, or type G. The pressure sore alleviating effects of the botulinum toxin may persist for between about 2 weeks (i.e. upon administration of a short acting botulinum toxin, such as a botulinum toxin type E or F) and 5 years (i.e. upon implantation of a controlled release botulinum toxin implant). The botulinum neurotoxin can be a recombinantly made botulinum neurotoxins, such as botulinum toxins produced by an *E. coli* bacterium. In addition or alternatively, the botulinum neurotoxin can be a modified neurotoxin, that is a botulinum neurotoxin which has at least one of its amino acids deleted, modified or replaced, as compared to a native or the modified botulinum neurotoxin can be a recombinant produced botulinum neurotoxin or a derivative or fragment thereof.

A method for treating a pressure sore according to the present invention can comprise the step of local administration of a botulinum toxin to a patient with a pressure sore to thereby alleviate the pressure sore. The botulinum toxin can be selected from the group consisting of botulinum toxin types A, B, C, D, E, F and G. Botulinum toxin type A is a preferred botulinum toxin.

A detailed embodiment of my invention can comprise a method for treating a pressure sore by local administration to a patient with a pressure sore of between about 1 unit and about 3,000 units of a botulinum toxin (for example between about 1-50 units of a botulinum toxin type A or between about 50 to 3,000 units of a botulinum toxin type B), thereby alleviating the pressure sore for between about two weeks and about 5 years.

My invention also encompasses a method for treating pressure sore by locally administering a botulinum toxin (such as a botulinum toxin type A, B, C, D, E, F or G, in an amount of from 1 unit to 3,000 units per treatment session) to a patient predisposed to developing a pressure sore, thereby preventing the patient from experiencing a pressure sore. A patient predisposed to pressure sore is a human who has pressure points due to immobilization, injury, hospitalization and the like. The local administration can be carried out by subcutaneous or by topical administration of the botulinum toxin a location on or within the skin of the patient where a pressure sore is located. The pressure sore can be reduced in size by from about 20% to 100%.

DESCRIPTION

The present invention is based upon the discovery that a pressure sore can be treated by local administration of a therapeutically effective amount of a Clostridial neurotoxin, such as a botulinum neurotoxin. The botulinum neurotoxin (such as a botulinum neurotoxin serotype A, B, $C_1$ D, E, F or G) can be administered by topical application or subdermal injection at and/or in the vicinity of a pressure sore of a patient. Alternately, the botulinum toxin can be administered to an intradermal or subdermal neuron to thereby downregulate, inhibit or suppress a neuronally mediated or influenced pressure sore.

Without wishing to be bound by theory, several mechanisms for the efficacy of treatment of pressure sores by my invention disclosed herein can be set forth. Firstly, a botulinum toxin can act to reduce the pain and inflammation symptoms of a pressure sore. This can occur due to the ability of a botulinum toxin to effect release of pain inducing neuropeptides such as substance-P, VIP and cGRP, which are involved in pain signal transmission.

Thus, application of botulinum toxin to the ulcerative area of a pressure sore can decrease or inhibit the inflammation and pain which accompanies a pressure sore. The inflammation can be due to the shearing and trauma from the pressure applied which results in the formation of microcirculatory occlusions as the applied pressure rises above capillary filling pressure. When this occurs ischemia, inflammation and tissue anoxia results. Tissue anoxia leads to cell death, necrosis, and ulceration.

Secondly, the skin inflammation symptom of a pressure sore comprises release of various mediators that can cause plasma extravasation, leaking, and weakening of blood vessels. In response, to the damaged vessels and the released inflammatory signals and mediators released, new blood vessels begin to arise and to infiltrate the area of the pressure sore. This blood vessel recruitment can be a function of the releasing of the mediators and the amount or degree of new blood vessel production could be proportional to their release. Therefore, practise of the method disclosed herein can inhibit the release of new blood vessel production mediators (by local administration of a botulinum toxin), and decrease recruitment of new blood vessels at the site of a pressure sore and thereby decrease development of the pressure sore.

Thirdly, by weakening muscles and reducing contractures and spasticity a botulinum toxin can reduce the effects of repeated application of pressure to one or more skin locations where skin tissues are repeatedly abraded due it joint flexation. Contractures rigidly hold a joint in flexion, while spasticity subjects tissues to considerable repeated friction and shear forces.

Fourthly, use of a botulinum toxin can inhibit release of acetylcholine and/or of another neurotransmitter or neuropeptide by one or more dermal nerves or structures which innervate or which influence a pressure sore, to thereby permit effective treatment of a pressure sore. Alternately, the administered Clostridial neurotoxin may have a direct effect upon the pressure sore. By effective treatment it is meant that the pressure sore becomes less painful, less inflamed and/or regresses (i.e. becomes smaller in size [i.e. thinner] or disappears altogether).

With regard to a proposed physiological mechanism for use of a Clostridial neurotoxin to treat a pressure sore as set forth herein, it is known that human keratinocytes can respond to acetylcholine. It is believed that acetylcholine is released by keratinocytes to function as a local hormone in the epidermis. Grando S. et al., *Human keratinocytes synthesize, secrete, and degrade acetylcholine*, J Invest Dermatol. July 1993; 101(1):32-6. Human epidermal keratinocytes possess cholinergic enzymes, which synthesize and degrade acetylcholine, and express both nicotinic and muscarinic classes of cholinergic receptors on their cell surfaces. These epidermal keratinocyte cell surface receptors bind acetylcholine and initiate various cellular responses. Significantly, the presence in keratinocytes of a functional cholinergic system suggests a role for acetylcholine in most, if not all, aspects of keratinocyte function. Acetylcholine employs calcium as a mediator for its effects on keratinocytes. In turn, changes in calcium concentration can affect expression and function of keratinocyte cholinergic enzymes and cholinergic receptors. At different stages of their differentiation, keratinocytes demonstrate unique combinations of cholinergic enzymes and cholinergic receptor types. Grando S., *Biological functions of keratinocyte cholinergic receptors*, J Investig Dermatol Symp Proc. August 1997; 2(1):41-8.

Importantly, skin innervation exerts influence on the proliferation of keratinocytes and the thickness of the epidermis. Huang et al., *Influence of cutaneous nerves on keratinocyte proliferation and epidermal thickness in mice. Neuroscience.* 1999; 94(3):965-73. Several lines of evidence suggest that nerves which terminate in the skin have profound influences on their target, the epidermis. See e.g. Grando S., *Biological functions of keratinocyte cholinergic receptors*; J Investig Dermatol Symp Proc. August 1997; 2(1):41-8; Grando S., et al., *Activation of keratinocyte nicotinic cholinergic receptors stimulates calcium influx and enhances cell differentiation*. Invest Dermatol. September 1996; 107(3):412-8; Ndoye A., et al., *Identification and mapping of keratinocyte muscarinic acetylcholine receptor subtypes in human epidermis*, J Invest Dermatol. September 1998; 111(3):410-6; Palacios J., et al., *Cholinergic neuropharmacology: an update*, Acta Psychiatr Scand Suppl. 1991; 366:27-33; Whitehouse P., et al., *Nicotinic and muscarinic cholinergic receptors in Alzheimer's disease and related disorders*, J Neural Transm Suppl. 1987; 24:175-82; Arredondo J., et al., *Central role of alpha7 nicotinic receptor in differentiation of the stratified squamous epithelium*, J Cell Biol. Oct. 28, 2002; 159(2):325-36; Andreadis S., et al., *Keratinocyte growth factor induces hyperproliferation and delays differentiation in a skin equivalent model system*, FASEB J. April 2001; 15(6):898-906; Krnjevic K., *Central cholinergic mechanisms and function*. Prog Brain Res. 1993; 98:285-92; *Epidermal expression of the full-length extracellular calcium-sensing receptor is required for normal keratinocyte differentiation*, J Cell Physiol. July 2002; 192(1):45-54; Grando S., et al., *Human keratinocytes synthesize, secrete, and degrade acetylcholine* J Invest Dermatol. July 1993; 101(1):32-6; Zia S., et al., *Receptor-mediated inhibition of keratinocyte migration by nicotine involves modulations of calcium influx and intracellular concentration*, J Pharmacol Exp Ther. June 2000; 293(3); 973-81; Nguyen V., eta., *Keratinocyte acetylcholine receptors regulate cell adhesion* Life Sci. Mar. 28, 2003; 72(18-19): 2081-5; Nguyen V., et al., *Programmed cell death of keratinocytes culminates in apoptotic secretion of a humectant upon secretagogue action of acetylcholine* J Cell Sci. March 2001; 114(Pt 6):1189-204; Grando S., et al., *Keratinocyte muscarinic acetylcholine receptors: Immunolocalization and partial characterization*, J Invest Dermatol. January 1995; 104(1):95-100; Lin Y., et al., (2001) *Cutaneous nerve terminal degeneration in painful mononeuropathy*, Experimental Neurology. 170(2):290-6; Pan C., et al., (2001) *Degeneration of nociceptive nerve terminals in human peripheral neuropathy*, Neuroreport. 12(4):787-92; Hsiung-F., et al., (2001) *Quantitative pathology of cutaneous nerve terminal degeneration in the human skin*, Acta Neuropathologica 102:455-461; Ko M., et al., *Cutaneous nerve degeneration induced by acrylamide in mice*, Neuroscience Letters. (2000)293(3):195-8; Lin Y., et al., *Quantitative sensory testing: normative values and its application in diabetic neuropathy*, Acta Neurol Taiwan 1998; 7:176-184; T. Huang, et al., *Influence of cutaneous nerves on keratinocyte proliferation and epidermal thickness in mice*, Neuroscience 94:965-973, 1999; Hsieh S., et al., *Pathology of nerve terminal degeneration in the skin*, Journal of Neuropathology & Experimental Neurology. 2000; 59(4):297-307; Huang I. et al., *Influence of cutaneous nerves on keratinocyte proliferation and epidermal thickness in mice*, Neuroscience. 1999; 94(3):965-73; Hsieh S., et al., *Modulation of keratinocyte proliferation by skin innervation*. Journal of Investigative Dermatology, 1999; 113(4):579-86, Chen W., et al., *Trophic interactions between sensory nerves and their targets*, Journal of Biomedical Science. 1999; 6(2):79-85; Chiang H-Y, et al., *Regional difference in epidermal thinning after skin denervation*, Exp Neurol 1998; 154(1):137-45; Hsieh S., et al., *Skin innervation and its influence on the epidermis*, J Biomed Sci 1997; 4: 264-268; Lee M., et al., *Clinical and electrophysiological characteristics of inflammatory demyelinating neuropathies*, Acta Neurol Taiwan 1997; 6:283-288; Wu T., et al., *Demonstration of human papillomavirus (HPV) genomic amplification and viral-like particles from CaSki cell fine in SCID mice*, J Virol Methods 1997; 65:287-298; Hsieh S., et al., *Epidermal denervation and its effects on keratinocytes and Langerhans cells*, J Neurocytol 1996; 25:513-524; McCarthy B., et al., *Cutaneous innervation in sensory neuropathies: evaluation by skin biopsy*, Neurol 1995; 45:1848-1855; Griffin J., et al., *Axonal degeneration and disorders of the axonal cytoskeleton*. In: Waxman S., et al., *The Axon*. New York: Oxford University Press, 1995:375-390.

Thus, it can be postulated that a botulinum toxin can be used to induce denervation and thereby can treat a pressure sore—by preventing (i.e. downregulating) the release of various neuropeptides released by nerves which innervate the skin. Among these neuropeptides are the tachykinins, substance P and neurokinin A, calcitonin gene-related peptide (CGRP), vasoactive intestinal peptide (VIP) and somatostatin, all of which have been reported to modulate skin cell functions such as cell proliferation. As set forth previously, release of most neurotransmitters and related neuropeptides can be blocked by botulinum toxin. See e.g. Hokfelt T., *Neuropeptides in perspective: The last ten years*, Neuron 1991; 7: 867-879; Xu Z-QD et al, *Galanin/GMAP- and NPY-like immunoreactivities in locus coeruleus and noradrenergic nerve terminals in the hippocampal formation and cortex with notes on the galanin-R1 and -R2 receptors*, J. Comp; Neurol. 1998; 392: 227-252; Xu Z-QD et al, *Galanin-5-hydroxytryptamine interactions: Electrophysiological, immunohistochemical and in situ hybridization studies on rat dorsal raphe neurons with a note on galanin R1 and R2 receptors*. Neuroscience 1998; 87: 79-94; Johnson M., *Synaptic glutamate release by postnatal rat serotonergic neurons in microculture*, Neuron 1994; 12: 433-442; Sneddon P., et al., *Pharamcological evidence that adenosine triphosphate and noradrenaline are cotransmitters in the guinea-pig vas deferens*. J. Physiol. 1984; 347: 561-580; Kaneko T., et al., *Immunohistochemical demonstration of glutaminase in catecholaminergic and serotonergic neurons of rat brain*, Brain Res. 1990; 507: 141-154; Kasakov L., et al., *Direct evidence for concomitant release of noradrenaline, adenosine 5'-triphosphate and neuropeptide Y from sympathetic nerve supplying the guinea-pig vas deferens*. J. Auton. Nerv. Syst. 1988; 22: 75-82; Nicholas A. et al., *Glutamate-like immunoreactivity in medulla oblongata catecholamine/substance P neurons*, NeuroReport 1990; 1: 235-238; Nicholas A. et al., Kupfermann I., *Functional studies of cotransmission*. Physiol. Rev. 1991; 71: 683-732.48: 545-59; Lundberg J., *Pharmacology of cotransmission in the autonomic nervous system: Integrative aspects on amines, neuropeptides, adenosine triphosphate, amino acids and nitric oxide*, Pharmacol. Rev. 1996; 48: 113-178; Hsieh S., et al., *Skin Innervation and Its Effects on the Epidermis*, J Biomed Sci. 1997; 4(5):264-268; Legat F., et al., *Repeated subinflammatory ultraviolet B irradiation increases substance P and calcitonin gene-related peptide content and augments mustard oil-induced neurogenic inflammation in the skin of rats*, Neurosci Lett. Sep. 6, 2002; 329(3):309-13; White S., Asahina A., et al., *Specific induction of cAMP in Langerhans cells by calcitonin gene-related peptide: relevance to functional effects*, Proc Natl Acad Sci USA. Aug. 29, 1995; 92(18):8323-7; Inaba N., et al., *Capsaicin-induced calcitonin gene-related peptide release from isolated rat stomach measured with a new chemiluminescent enzyme immunoassay*, Jpn J Pharmacol. November 1996; 72(3):223-9; Hosoi J., et al., *Regulation of Langerhans cell function by nerves containing calcitonin gene-related peptide*, Nature. May 13, 1993; 363(6425):159-63.

FIG. 1 illustrates a mechanism of action of a botulinum toxin ("Btx" in FIG. 1). A botulinum toxin can inhibit release of cGRP, SP, and glutamate from dermal sensory nerves, and also inhibit direct release of these mediators from skin keratinocyte, endothelial and melanocyte cells. It is known that neuropeptides released by sensory nerves that innervate the skin and contact epidermal and dermal cells can directly modulate functions of keratinocytes, Langerhans cells (LC), mast cells, dermal microvascular endothelial cells and infiltrating immune cells. In FIG. 1 NO is nitrous oxide, cGRP is calcitonin gene-related peptide, Ach is acetylcholine, cGRP-R is the receptor for the cGRP molecule, v-dil means vasodilation and SP is substance P.

My invention includes methods for treating at least the following types of pressure sores; decubitus ulcers, ulcers of the heel of the foot, ulcer of the shoulder, ulcers caused by any part of the body that can exert an effective amount of pressure so as to create a condition suitable for ulcer formation, optimally treating in but not limited to: stage I or stage II of the National Pressure Ulcer Advisory Panel classification system. A botulinum toxin can be applied in an effective therapeutic amount by applying about one unit of a botulinum toxin type A/cm2 of the affected area. Methods to apply the botulinum toxin includes but not limited to subcutaneous, intradermal, intramuscular, topical, and via slow or expended release implants. A botulinum toxin can be applied as a single agent, or in combination with a bacteriostatic agent, antibiotic cream or emollient, or any other agent that may be considered to be used in the management of ulcers.

According to my invention, a botulinum toxin can be used alone or in combination with another agents with one ore more dressings and occlusives: Stage II ulcers confined to the epidermis or dermis can be treated with a hydrocolloid occlusive dressing (DuoDerm), which maintains a moist environment to facilitate reepithelialization. For more advanced ulcers, a large variety of treatment options is available. These include wet-to-dry dressings, incorporating isotonic sodium chloride solution or dilute Dakins solution (sodium hypochlorite), Silvadene, Sulfamylon, hydrogels (Carrington gel), xerogels (Sorbsan), and vacuum-assisted closure (VAC) sponges.

A botulinum toxin used alone or in combination with above agents may also be used along with the following non-limiting examples body support: specialized support surfaces are available for bedding and wheelchairs, which can maintain tissues at pressures below 30 mm Hg. These specialized surfaces include foam devices, air-filled devices, low-airloss beds (Flexicair, KinAir), and air-fluidized beds (Clinitron, FluidAir). Low-airloss beds support the patient on multiple inflatable air-permeable pillows. Air-fluidized beds suspend the patient as air is pumped into an air-permeable mattress containing millions of microspheric uniformly sized silicone-coated beads.

Thus, my invention includes use of a botulinum toxin to treat a pressure sore by causing it to regress (become smaller) and/or to relieve the pain and inflammation that can accompany a pressure sore.

The amount of the Clostridial toxin administered according to a method within the scope of the disclosed invention can vary according to the particular characteristics of the pressure sore being treated, including its severity and other various patient variables including size, weight, age, and responsiveness to therapy. To guide the practitioner, typically, no less than about 5 units and no more than about 500 units of a botulinum toxin type A (such as BOTOX®) is administered per injection site (i.e. to each pressure sore location injected), per patent treatment session. For a botulinum toxin type A such as DYSPORT®, preferably no less than about 10 units and no more about 2000 units of the botulinum toxin type A are administered per administration or injection site, per patent treatment session. For a botulinum toxin type B such as MYOBLOC®, preferably no less than about 200 units and no more about 25000 units of the botulinum toxin type B are administered per administer or injection site, per patent treatment session. Less than about 5, 10 or 200 units (of BOTOX®, DYSPORT® and MYOBLOC® respectively) can fail to achieve a desired therapeutic effect, while more than about 500, 2000 or 25000 units (of BOTOX®, DYSPORT® and MYOBLOC® respectively) can result in clinically observable and undesired muscle hypotonicity, weakness and/or paralysis.

More preferably: for BOTOX® no less than about 10 units and no more about 400 units of a botulinum toxin type A; for DYSPORT® no less than about 30 units and no more than about 1600 units, and; for MYOBLOC®, no less than about 250 units and no more than about 20000 units are, respectively, administered per injection site, per patent treatment session.

Most preferably: for BOTOX® no less than about 20 units and no more about 300 units of a botulinum toxin type A; for DYSPORT® no less than about 60 units and no more than about 1200 units, and; for MYOBLOC®, no less than about 1000 units and no more than about 15000 units are, respectively, administered per injection site, per patent treatment session. It is important to note that there can be multiple injection sites (i.e. a pattern of injections) for each patient treatment session.

Although examples of routes of administration and dosages are provided, the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14th edition, published by McGraw Hill). For example, the route and dosage for administration of a Clostridial neurotoxin according to the present disclosed invention can be selected based upon criteria such as the solubility characteristics of the neurotoxin chosen as well as the intensity and scope of a pressure sore.

The present invention is based on the discovery that local administration of a Clostridial toxin can provide significant and long lasting relief from a pressure sore. A Clostridial toxin used in accordance with the invention disclosed herein can inhibit transmission of chemical or electrical signals between select neuronal groups that are involved in generation of a pressure sore. The Clostridial toxins preferably are not cytotoxic to the cells that are exposed to the Clostridial toxin. The Clostridial toxin can inhibit neurotransmission by reducing or preventing exocytosis of neurotransmitter from the neurons exposed to the Clostridial toxin. Or the applied Clostridial toxin can reduce neurotransmission by inhibiting the generation of action potentials of the neurons exposed to the toxin. The pressure sore alleviation effect provided by the Clostridial toxin can persist for a relatively long period of time, for example, for more than two months (or for 2-4 weeks upon use of a botulinum toxin type E or F), and potentially for several years.

Examples of Clostridial toxins within the scope of the present invention include neurotoxins made by *Clostridium botulinum, Clostridium butyricum* and *Clostridium beratti* species. In addition, the botulinum toxins used in the methods of the invention can be a botulinum neurotoxin selected from a group of botulinum toxin types A, B, $C_1$, D, E, F, and G. In one embodiment of the invention, the botulinum neurotoxin administered to the patient is botulinum toxin type A. Botulinum toxin type A is desirable due to its high potency in humans, ready availability, and known use for the treatment of skeletal and smooth muscle disorders when locally administered by Intramuscular injection. The present invention also includes the use of (a) Clostridial neurotoxins obtained or processed by bacterial culturing, toxin extraction, concentration, preservation, freeze drying, and/or reconstitution; and/or (b) modified or recombinant neurotoxins, that is neurotoxins that have had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made. These neurotoxin variants retain the ability to inhibit neurotransmission between or among neurons, and some of these variants may provide increased durations of inhibitory effects as compared to native neurotoxins, or may provide enhanced binding specificity to the neurons exposed to the neurotoxins. These neurotoxin variants may be selected by screening the variants using conventional assays to identify neurotoxins that have the desired physiological effects of inhibiting neurotransmission.

Botulinum toxins for use according to the present invention can be stored in lyophilized, vacuum dried form in containers under vacuum pressure or as stable liquids. Prior to lyophilization the botulinum toxin can be combined with pharmaceutically acceptable excipients, stabilizers and/or carriers, such as albumin. The lyophilized material can be reconstituted with saline or water to create a solution or composition containing the botulinum toxin to be administered to the patient.

Although the composition may only contain a single type of neurotoxin, such as botulinum toxin type A, as the active ingredient to suppress neurotransmission, other therapeutic compositions may include two or more types of neurotoxins, which may provide enhanced therapeutic treatment of a pressure sore. For example, a composition administered to a patient may include botulinum toxin type A and botulinum toxin type B. Administering a single composition containing two different neurotoxins can permit the effective concentration of each of the neurotoxins to be lower than if a single neurotoxin is administered to the patient while still achieving the desired therapeutic effects. The composition administered to the patient may also contain other pharmaceutically active ingredients, such as, protein receptor or ion channel modulators, in combination with the neurotoxin or neurotoxins. These modulators may contribute to the reduction in neurotransmission between the various neurons. For example, a composition may contain gamma aminobutyric acid (GABA) type A receptor modulators that enhance the inhibitory effects mediated by the GABAA receptor. The GABAA receptor inhibits neuronal activity by effectively shunting current flow across the cell membrane. GABAA receptor modulators may enhance the inhibitory effects of the GABAA receptor and reduce electrical or chemical signal transmission from the neurons. Examples of GABAA receptor modulators include benzodiazepines, such as diazepam, oxaxepam, lorazepam, prazepam, alprazolam, halazeapam, chordiazepoxide, and chlorazepate. Compositions may also contain glutamate receptor modulators that decrease the excitatory effects mediated by glutamate receptors. Examples of glutamate receptor modulators include agents that inhibit current flux through AMPA, NMDA, and/or kainate types of glutamate receptors. The compositions may also include agents that modulate dopamine receptors, such as antipsychotics, norepinephrine receptors, and/or serotonin receptors. The compositions may also include agents that affect ion flux through voltage gated calcium channels, potassium channels, and/or sodium channels. Thus, the compositions used to treat a pressure sore can include one or more neurotoxins, such as botulinum toxins, in addition to ion channel receptor modulators that may reduce neurotransmission.

The neurotoxin may be administered by any suitable method as determined by the attending physician. The methods of administration permit the neurotoxin to be administered locally to a selected target tissue. Methods of administration include injection of a solution or composition containing the neurotoxin, as described above, and include implantation of a controlled release system that controllably releases the neurotoxin to the target tissue. Such controlled release systems reduce the need for repeat injections. Diffusion of biological activity of a botulinum toxin within a tissue appears to be a function of dose and can be graduated. Jankovic J., et al *Therapy With Botulinum Toxin*, Marcel Dekker, Inc., (1994), page 150. Thus, diffusion of botulinum toxin can be controlled to reduce potentially undesirable side effects that may affect the patient's cognitive abilities. For example, the neurotoxin can be administered so that the neurotoxin primarily effects neural systems believed to be involved in the generation of a pressure sore.

A polyanhydride polymer, Gliadel® (Stolle R & D, Inc., Cincinnati, Ohio) a copolymer of poly-carboxyphenoxypropane and sebacic acid in a ratio of 20:80 has been used to make implants, and has been intracranially implanted to treat malignant gliomas. Polymer and BCNU can be co-dissolved in methylene chloride and spray-dried into microspheres. The microspheres can then be pressed into discs 1.4 cm in diameter and 1.0 mm thick by compression molding, packaged in aluminum foil pouches under nitrogen atmosphere and sterilized by 2.2 megaRads of gamma irradiation. The polymer permits release of carmustine over a 2-3 week period, although it can take more than a year for the polymer to be largely degraded. Brem, H., et al. *Placebo-Controlled Trial of Safety and Efficacy of Intraoperative Controlled Delivery by Biodegradable Polymers of Chemotherapy for Recurrent Gliomas*, Lancet 345; 1008-1012:1995.

Implants useful in practicing the methods disclosed herein may be prepared by mixing a desired amount of a stabilized neurotoxin (such as non-reconstituted BOTOX®) into a solution of a suitable polymer dissolved in methylene chloride. The solution may be prepared at room temperature. The solution can then be transferred to a Petri dish and the methylene chloride evaporated in a vacuum desiccator. Depending upon the implant size desired and hence the amount of incorporated neurotoxin, a suitable amount of the dried neurotoxin incorporating implant is compressed at about 8000 p.s.i. for 5 seconds or at 3000 p.s.i. for 17 seconds in a mold to form implant discs encapsulating the neurotoxin. See e.g. Fung L. K. et al., *Pharmacokinetics of Interstitial Delivery of Carmustine 4-Hydroperoxycyclophosphamide and Paclitaxel From a Biodegradable Polymer Implant in the Monkey Brain*, Cancer Research 58; 672-684:1998.

Local administration of a Clostridial toxin, such as a botulinum toxin, can provide a high, local therapeutic level of the toxin. A controlled release polymer capable of tong term, local delivery of a Clostridial toxin to a target pressure sore location permits effective dosing of the target tissue. A suitable implant, as set forth in U.S. Pat. No. 6,306,423 entitled "Neurotoxin Implant", allows the direct introduction of a chemotherapeutic agent to a target tissue via a controlled release polymer. The implant polymers used are preferably hydrophobic so as to protect the polymer incorporated neurotoxin from water induced decomposition until the toxin is released into the target tissue environment.

Local administration of a botulinum toxin, according to the present invention, by injection or implant to a target tissue provides a superior alternative to systemic administration of pharmaceuticals to patients to alleviate a pressure sore.

The amount of a Clostridial toxin selected for local administration to a target tissue according to the present disclosed invention can be varied based upon criteria such as the severity of the pressure sore being treated, solubility characteristics of the neurotoxin toxin chosen as well as the age, sex, weight and health of the patient. For example, the extent of the area of skin influenced is believed to be proportional to the volume of neurotoxin injected, while the quantity of the pressure sore suppressant effect is, for most dose ranges, believed to be proportional to the concentration of a Clostridial toxin administered. Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14th edition, published by McGraw Hill).

Significantly, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assessed using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality, and general health perceptions. Scores obtained can be compared to published values available for various general and patient populations.

EXAMPLES

The following non-limiting examples provide those of ordinary skill in the art with specific preferred methods to treat conditions within the scope of the present invention and are not intended to limit the scope of the invention. In the following examples various modes of non-systemic administration of a Clostridial neurotoxin can be carried out. For example, by topical application (cream or transdermal patch), subcutaneous injection, or by implantation of a controlled release implant.

Example 1

Use of a Botulinum Toxin to Treat Pressure Sores Which Develop Subsequent to Surgery A 52 year old woman weighing 42 kg is diagnosed with carcinoma of the vulva. She is otherwise fit and active. She smokes 20 cigarettes a day. She has a radical vulvectomy and bilateral inguinal lymphadenectomy under combined general and epidural anesthesia. She is given 20 ml of 0.25% bupivacaine for epidural anaesthesia. In an attempt to prevent pressure sores, the operating table is covered with silicon jelly pads. The surgery lasts about three hours. The patient is supine for the first 90 minutes and in the lithotomy position thereafter. Her preoperative blood pressure is 120/70 mm Hg. During surgery her systolic blood pressure varies between 85 and 90 mm Hg and her general condition is stable. She receives a continuous epidural infusion of plain 0.15% bupivacaine for postoperative analgesia. She remains free of pain and is comfortable during the surgery. After the surgery her systolic blood pressure can vary between 75 and 85 mm Hg. She is unable to move her legs on the first postoperative day, but can move them on the second day. On the third day, the epidural is discontinued, and she could get out of bed and walk. On the fourth day she notices blisters and small areas of discoloration on her heels. Over the next three days the blisters developed into ulcers. Five weeks later at outpatient follow up her heels were worse, with severe pressure necrosis of both heels. Typically such pressure sore can take eight to nine months to heal. She is administered 40 units of a botulinum toxin type A over five injection sites (8 units per injection site per foot) on each heel (80 units total botulinum toxin administration per treatment session). Within 1-7 days a reduction of both inflammation and pain is reported by the patient at the sites of her heel ulcers. The treatment is repeated after 10 weeks. Within four months pressure sores completely heal.

Example 2

Use of a Botulinum Toxin to Treat Pressure Sores Related to Diabetes

A 72-year-old male with diabetes develops four stage III pressure sores (located on his sacrum, both left trochanter, and at both heels) after a cerebral infarction caused tetraplegia. He is hospitalized for treatment of hyperglycemia (400 mg/dL) and a high fever caused by wound infection. Black necrotic tissue in the sacral and trochanteric ulcers is partially resected, and the wounds are packed with gauze soaked in povidone-iodine. This wound treatment continued for 3 months, with no resolution of the pressure sores. Given the patients' diabetic state and non-surgical status, a course of botulinum toxin A is recommended for his pressure sores. A total of 200 U is administered intradermally as about 1 unit/cm2 by administering a total of 50 units to four sites at his sacrum (12.5 units at each site), a total 50 units at two sites in his trochanter (25 units at each site), and total of 50 units at two sites on for each heel (25 units at each heel injection site).

After 2 weeks, bleeding and pain ceases. New granulation tissue begins to form within the ulcers. After the necrotic tissue is removed, PV film dressing is used to cover the sacral and trochanteric wounds. Six weeks later all four pressure sores have become reduced in size significantly, with only the sacral ulcer still visible.

Example 3

Use of a Botulinum Toxin to Treat Pressure Sores Related to Spasticity

An 87-year-old female develops a stage II sacral pressure ulcer during hospitalization for a cerebral infarction. As a result of the stroke, the patient has spastic lower limbs, that contracted limbs, creating pressure on both heels. In order to prevent further onset of ulcers, the patients spasticity is treated with 400 units of a botulinum toxin type A divided into 200 units per limb, which was distributed in four sites intramuscular per limb. In addition, 50 units of a botulinum toxin type A is injected subcutaneously into the region of the stage II ulcers, dividing into two sites per heel. Four weeks later the patient's spasms are significantly reduced, both ulcers were significantly reduced, and patient reported no pain. Six weeks later, patient still had reduction in spasm, and no noticeable signs of pressure sores.

Example 4

Use of a Botulinum Toxin to Treat Pressure Sores Related to Immobility

An 43 year old woman is admitted following a fall from a ten story building. Two months post admission the patient begins to develop significant pain and tenderness in her sacral region. On admission to rehabilitation, the patient is evaluated and placed on a stage III mattress overlay. Prior to this the patient has been lying prone since her admission to acute care. It is recommended that the patient begin a course of botulinum toxin to prevent progression to stage IV pressure sores. After debridement, 100 units of a botulinum toxin type A admixed into vehicle comprised of bacitracin ointment and is applied topically in a concentration of 1 unit/ml of ointment and applied as 1 unit botulinum toxin/cm2. Four 4 weeks later, significant reduction in size of the pressure sore is noted, and pain and discomfort are absent. Six weeks later the patient is able to move around in the bed with no discomfort.

Example 5

Use of a Botulinum Toxin to Prevent Development of Pressure Sores Subsequent to Surgery A successful initial bladder closure is carried out upon a 52 year old male patient and steps are taken to ensure development of adequate bladder capacity and ultimate continence in this patient with bladder exstrophy. As secure pelvic fixation is essential to post operative success, the patent is fitted with and into pelvic and extremity immobilization devices. Thus, the patient is immobilized with an external fixator and 6 to 8 weeks of modified Buck's traction with osteotomy. To prevent development of pressure sores he is administered 40 units of a botulinum toxin type A over five injection sites on his buttocks (8 units per injection site) and 40 units of a botulinum toxin type A over five injection sites on his heels (8 units per injection site) (80 units total botulinum toxin administration per treatment session). These injection sites are chosen as the likely sites at which pressure sores can develop. No inflammation, pain or pressure sores develop on his buttocks or heels.

In each of the examples above a botulinum toxin type B, C, D, E, F or G can be substituted for the botulinum toxin type A used above, for example by use of 250 units of a botulinum toxin type B. The specific amount of a botulinum toxin (such as BOTOX®) administered depends upon a variety of factors to be weighed and considered within the discretion of the attending physician and in each of the examples insignificant amounts of botulinum toxin enter appear systemically with no significant side effects.

A method for treating a pressure sore according to the invention disclosed herein has many benefits and advantages, including the following:

1. the symptoms of a pressure sore can be dramatically reduced or eliminated.

2. the symptoms of a pressure sore can be reduced or eliminated for at least about two weeks to about six months per injection of neurotoxin and for from about one year to about five years upon use of a controlled release neurotoxin implant.

3. the injected or implanted Clostridial neurotoxin shows little or no tendency to diffuse or to be transported away from the intramuscular (or intradermal or subdermal) injection or implantation site.

4. few or no significant undesirable side effects occur from intramuscular (or intradermal or subdermal) injection or implantation of the Clostridial neurotoxin.

5. the present methods can result in the desirable side effects of greater patient mobility, a more positive attitude, and an improved quality of life.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes local administration methods to alleviate a pressure sore wherein two or more neurotoxins, such as two or more botulinum toxins, are administered concurrently or consecutively. For example, botulinum toxin type A can be administered until a loss of clinical response or neutralizing antibodies develop, followed by administration of botulinum toxin type B. Alternately, a combination of any two or more of the botulinum serotypes A-G can be locally administered to control the onset and duration of the desired therapeutic result. Furthermore, non-neurotoxin compounds can be administered prior to, concurrently with or subsequent to administration of the neurotoxin to proved adjunct effect such as enhanced or a more rapid onset of denervation before the neurotoxin, such as a botulinum toxin, begins to exert its therapeutic effect.

A botulinum toxin can be administered by itself or in combination of one or more of the other botulinum toxin serotypes. The botulinum toxin can be a recombinantly made or a hybrid botulinum toxin.

My invention also includes within its scope the use of a neurotoxin, such as a botulinum toxin, in the preparation of a medicament for the treatment of a pressure sore, by local administration of the neurotoxin.

All references, articles, patents, applications and publications set forth above are incorporated herein by reference in their entireties.

Accordingly, the spirit and scope of the following claims should not be limited to the descriptions of the preferred embodiments set forth above.

I claim:

1. A method for treating a pressure sore in a patient, the method comprising the step of locally administering via subcutaneous injection a therapeutically effective amount of botulinum toxin type A to one or more sites of a pressure sore area or one or more sites in the vicinity of a pressure sore area on a patient in need thereof; wherein the pressure sore is a result of immobility of the patient; wherein the total amount of the botulinum toxin type A administered to the patient is between 1 unit and 10 units per kilogram; and wherein the therapeutically effective amount of the botulinum toxin type A administered to each site is less than an amount of botulinum toxin type A that would be used to paralyze a muscle.

2. A method for treating a pressure sore in a patient, the method comprising the step of locally administering via subcutaneous injection a therapeutically effective amount of botulinum toxin type A to one or more sites of a pressure sore area of a pressure sore area on a patient in need thereof; wherein the pressure sore is a result of immobility of the patient; wherein the total amount of the botulinum toxin type A administered to the patient is between 1 unit and 10 units per kilogram; and wherein the therapeutically effective amount of the botulinum toxin type A administered to each site is less than an amount of botulinum toxin type A that would be used to paralyze a muscle.

3. A method for treating a pressure sore in a patient, the method comprising the step of locally administering via subcutaneous injection a therapeutically effective amount of botulinum toxin type to one or more sites of a pressure sore area or one or more sites in the vicinity of a pressure sore area on a patient having a pressure sore that developed as a result of immobility of the patient, wherein the pressure sore is located at a site selected from the group consisting a heel, a sacrum, a shoulder and a trochanter; wherein the total amount of the botulinum toxin administered to the patient is between 1 unit and 10 units per kilogram; and wherein the therapeutically effective amount of the botulinum toxin administered to each site is less than an amount of botulinum toxin that would be used to paralyze a muscle.

4. The method of claim 3, wherein the botulinum toxin is a botulinum toxin type A.

\* \* \* \* \*